US008696905B2

(12) United States Patent
Coull et al.

(10) Patent No.: US 8,696,905 B2
(45) Date of Patent: *Apr. 15, 2014

(54) FLUID CONCENTRATOR

(75) Inventors: Thomas Coull, Rancho Palos Verdes, CA (US); Matthew R. Kyle, Plymouth, MN (US); Louis S. Kidder, Edina, MN (US)

(73) Assignee: Circle Biologics, Inc., Minneapolis, MN (US)

( * ) Notice: Subject to any disclaimer, the term of this patent is extended or adjusted under 35 U.S.C. 154(b) by 111 days.

This patent is subject to a terminal disclaimer.

(21) Appl. No.: 13/219,193

(22) Filed: Aug. 26, 2011

(65) Prior Publication Data

US 2012/0074073 A1    Mar. 29, 2012

Related U.S. Application Data

(63) Continuation of application No. 12/817,734, filed on Jun. 17, 2010, now Pat. No. 8,012,351, which is a continuation of application No. 11/932,125, filed on Oct. 31, 2007, now Pat. No. 7,740,760, which is a continuation of application No. 11/063,142, filed on Feb. 22, 2005, now Pat. No. 7,354,515.

(60) Provisional application No. 60/546,810, filed on Feb. 23, 2004.

(51) Int. Cl.
*B01D 63/02* (2006.01)
*B01D 61/14* (2006.01)
*B01D 61/18* (2006.01)
*B01D 24/32* (2006.01)
*B01D 61/22* (2006.01)

(52) U.S. Cl.
USPC ............... 210/321.79; 210/500.23; 210/781; 210/782; 210/360.1; 210/360.2; 210/378; 210/321.67; 210/321.68; 210/321.88

(58) Field of Classification Search
None
See application file for complete search history.

(56) References Cited

U.S. PATENT DOCUMENTS

| 3,669,789 A | 6/1972 | Berriman |
| 4,230,564 A | 10/1980 | Keefer |
| 4,886,597 A | 12/1989 | Wild et al. |
| 5,165,938 A | 11/1992 | Knighton |
| 5,405,607 A | 4/1995 | Epstein |
| 5,663,051 A | 9/1997 | Vlasselaer |
| 5,674,394 A | 10/1997 | Whitmore |

(Continued)

OTHER PUBLICATIONS

Cell Factor Technologies, Inc., 2004, GPS Platelet Concentration System, 10 pages.

(Continued)

*Primary Examiner* — Krishnan S Menon
(74) *Attorney, Agent, or Firm* — Merchant & Gould P.C.

(57) ABSTRACT

A concentrator is used for concentrating a fluid, particularly a plasma component out of blood, for treatment of a patient. The concentrator apparatus includes a main housing defining a centrifuge chamber, that also holds the filter. The concentrator allows viewing of the fluid after centrifuging, with an outlet port positionable at a height corresponding to the level of the fraction of the fluid to be further concentrated. Once the fluid is centrifuged, a portion of the fluid is drawn through the outlet, and then pressured past the filter to further concentrate the fluid using the same vessel as used for centrifuging. The same plunger is preferably used to draw centrifuged fluid from the centrifuge chamber as to pressure the centrifuged fluid past the filter.

21 Claims, 8 Drawing Sheets

(56) References Cited

U.S. PATENT DOCUMENTS

| | | |
|---|---|---|
| 5,733,545 A | 3/1998 | Hood, III |
| 5,788,662 A | 8/1998 | Antanavich et al. |
| 5,840,502 A | 11/1998 | Van Vlasselaer |
| 5,876,321 A | 3/1999 | Hlavinka et al. |
| 5,879,280 A | 3/1999 | Hlavinka et al. |
| 5,891,347 A | 4/1999 | Matsumoto |
| 5,935,437 A | 8/1999 | Whitmore |
| 6,001,259 A | 12/1999 | Whitmore |
| 6,010,627 A | 1/2000 | Hood, III |
| 6,027,655 A | 2/2000 | Holm |
| 6,063,297 A | 5/2000 | Antanavich et al. |
| 6,071,422 A | 6/2000 | Hlavinka et al. |
| 6,106,727 A | 8/2000 | Krasnoff et al. |
| 6,132,613 A | 10/2000 | Hopkin et al. |
| 6,197,194 B1 | 3/2001 | Whitmore |
| 6,207,066 B1 | 3/2001 | Trese et al. |
| 6,214,338 B1 | 4/2001 | Antanavich et al. |
| 6,299,784 B1 | 10/2001 | Biesel |
| 6,342,157 B1 | 1/2002 | Hood, III |
| 6,354,986 B1 | 3/2002 | Hlavinka et al. |
| 6,398,972 B1 | 6/2002 | Blasetti et al. |
| 6,524,568 B2 | 2/2003 | Worden |
| 6,582,350 B2 | 6/2003 | Dolecek |
| 6,582,386 B2 | 6/2003 | Min et al. |
| 6,596,180 B2 | 7/2003 | Baugh et al. |
| 6,706,008 B2 | 3/2004 | Vishnoi et al. |
| 6,716,187 B1 | 4/2004 | Jorgensen et al. |
| 6,790,371 B2 | 9/2004 | Dolecek |
| 6,793,828 B2 | 9/2004 | Dolecek et al. |
| 6,808,503 B2 | 10/2004 | Farrell et al. |
| 6,855,263 B2 | 2/2005 | Trese et al. |
| 6,884,228 B2 | 4/2005 | Brown et al. |
| 7,077,273 B2 | 7/2006 | Ellsworth et al. |
| 7,223,346 B2 | 5/2007 | Dorian et al. |
| 7,314,460 B2 | 1/2008 | Tu et al. |
| 7,354,515 B2 | 4/2008 | Coull et al. |
| 7,374,678 B2 | 5/2008 | Leach et al. |
| 7,413,652 B2 | 8/2008 | Dolecek et al. |
| 7,452,344 B2 | 11/2008 | Jorgensen et al. |
| 7,470,371 B2 | 12/2008 | Dorian et al. |
| 7,481,941 B2 | 1/2009 | Tsai et al. |
| 7,547,272 B2 | 6/2009 | Ellsworth et al. |
| 7,608,258 B2 | 10/2009 | Mishra |
| 7,694,828 B2 | 4/2010 | Swift et al. |
| 7,695,627 B2 | 4/2010 | Bosch et al. |
| 7,740,760 B2 | 6/2010 | Coull et al. |
| 7,766,900 B2 | 8/2010 | Leach et al. |
| 7,780,860 B2 | 8/2010 | Higgins et al. |
| 7,803,279 B2 | 9/2010 | Coull et al. |
| 7,806,276 B2 | 10/2010 | Leach et al. |
| 7,806,845 B2 | 10/2010 | Arm et al. |
| 7,811,463 B2 | 10/2010 | Dolecek et al. |
| 7,811,607 B2 | 10/2010 | Baugh et al. |
| 7,824,559 B2 | 11/2010 | Dorian et al. |
| 7,833,185 B2 | 11/2010 | Felt et al. |
| 7,838,039 B2 | 11/2010 | Baugh et al. |
| 7,845,499 B2 | 12/2010 | Higgins et al. |
| 7,866,485 B2 | 1/2011 | Dorian et al. |
| 7,867,159 B2 | 1/2011 | Dolecek et al. |
| 7,897,054 B2 | 3/2011 | Dolecek et al. |
| 7,914,689 B2 | 3/2011 | Higgins et al. |
| 7,954,646 B2 | 6/2011 | Leach et al. |
| 8,012,351 B2 | 9/2011 | Coull et al. |
| 2003/0205538 A1* | 11/2003 | Dorian et al. ............ 210/787 |
| 2004/0132003 A1 | 7/2004 | Dolecek et al. |
| 2004/0182795 A1 | 9/2004 | Dorian et al. |
| 2006/0060521 A1 | 3/2006 | Harms et al. |
| 2008/0108931 A1 | 5/2008 | Bobroff |
| 2008/0166421 A1 | 7/2008 | Buhr et al. |
| 2009/0220482 A1 | 9/2009 | Higgins et al. |
| 2010/0135969 A1 | 6/2010 | Mishra |

OTHER PUBLICATIONS

Harvest Technologies Corp., 2002, Developing Technologies for Accelerating Healing, Naturally, 6 pages.

Medtronic Biologic Therapeutics & Diagnostics, 2002, Magellan Autologous Platelet Separator, 6 pages.

SpectrumLabs.Com., 2002 "The ABCs of Filtration and Bioprocessing for the Third Millennium", "The ABCs of Filtration".

* cited by examiner

FLUID CONCENTRATOR

CROSS-REFERENCE TO RELATED APPLICATION(S)

This application is a continuation application of U.S. application Ser. No. 12/817,734, now U.S. Pat. No. 8,012,351, filed Jun. 17, 2010, which is a continuation application of U.S. application Ser. No. 11/932,125, now U.S. Pat. No. 7,740,760, filed Oct. 31, 2007, which is a continuation application of U.S. application Ser. No. 11/063,142, now U.S. Pat. No. 7,354,515, filed Feb. 22, 2005, which claims priority from Provisional Application No. 60/546,810 filed Feb. 23, 2004, entitled BUFFY COAT CONCENTRATOR APPARATUS AND METHOD, all of which are hereby incorporated by reference in their entirety.

BACKGROUND OF THE INVENTION

The present invention is directed to devices and methods for concentrating fluids. More particularly, the present invention is directed to devices and methods for concentrating body fluids such as blood, with the concentration steps including both a centrifugation act and a filtration act.

Concentration and/or filtration of body fluids has long been practiced in the medical arts. Of the various body fluids which may be concentrated or filtered, blood is perhaps the most common. Blood is commonly filtered to remove impurities or waste products (kidney dialysis, for example). Blood is commonly concentrated into different components, such as white blood cells, plasma, or red blood cells, for use in a wide variety of handling options and treatment modalities. In some instances, the filtration or concentration of blood components is not critically time sensitive, but rather can be carried out over a period of hours or days. In other instances, particularly when a patient's own blood is being filtered and/or concentrated and then immediately returned to the patient's body, the filtration and/or concentration process must be completed in a more time sensitive manner, such as within a matter of minutes. The present invention is particularly appropriate for use in time sensitive situations, and to reduce the handling time as compared to the prior art.

In some applications, the filtration and/or concentration process is carried out in an ongoing, streaming process, wherein the body fluid is simultaneously removed from the patient's body and then downstream returned to the patient's body. In other applications, the filtration and/or concentration process is carried out in a batch process, wherein an amount of the body fluid is removed from the body as a unit, treated, and then returned to the patient's body as a unit. The present invention is particularly intended for batch processing.

For body fluids which can be treated in a batch process, centrifugation is a common method of concentration. For example, a batch of blood may be removed as a unit and placed into a centrifuge vessel. The centrifuge vessel is spun at high speed, subjecting the blood to a centrifugal force which can be tens or hundreds of times the force of gravity. Under this centrifugal force, the blood separates into different components based to an extent on molecular weight, such as separation of red blood cells, platelet poor plasma, and an intermediate plasma fraction known as "buffy coat".

More recently, blood fractions separated by centrifugation have been further filtered to increase cell or component concentrations in the filtrate. U.S. Pat. Nos. 5,733,545, 6,010,627 and 6,342,157 to Hood, III show examples of this, and are incorporated by reference. Such concentrated, centrifuged body fluids have been shown to be useful in various treatment modalities, such as applying the concentrated blood component directed to an orthopedic wound site. However, the methods and devices taught in these Hood, III patents have shortcomings which have prevented widespread acceptance and use in an operating environment.

BRIEF SUMMARY OF THE INVENTION

The present invention is an apparatus and method for concentrating a fluid, particularly a plasma component out of blood, for treatment of a patient. The concentrator apparatus includes a main housing defining a centrifuge chamber, that also holds the filter. Once the fluid is centrifuged, a portion of the fluid is drawn past the filter to further concentrate the fluid using the same vessel as used for centrifuging. The same plunger is preferably used to draw centrifuged fluid from the centrifuge chamber at a selected height, and then reversed to pressure the centrifuged fluid past the filter.

While the above-identified drawing figures set forth preferred embodiments, other embodiments of the present invention are also contemplated, some of which are noted in the discussion. In all cases, this disclosure presents the illustrated embodiments of the present invention by way of representation and not limitation. Numerous other minor modifications and embodiments can be devised by those skilled in the art which fall within the scope and spirit of the principles of this invention.

DETAILED DESCRIPTION

Figure 1:
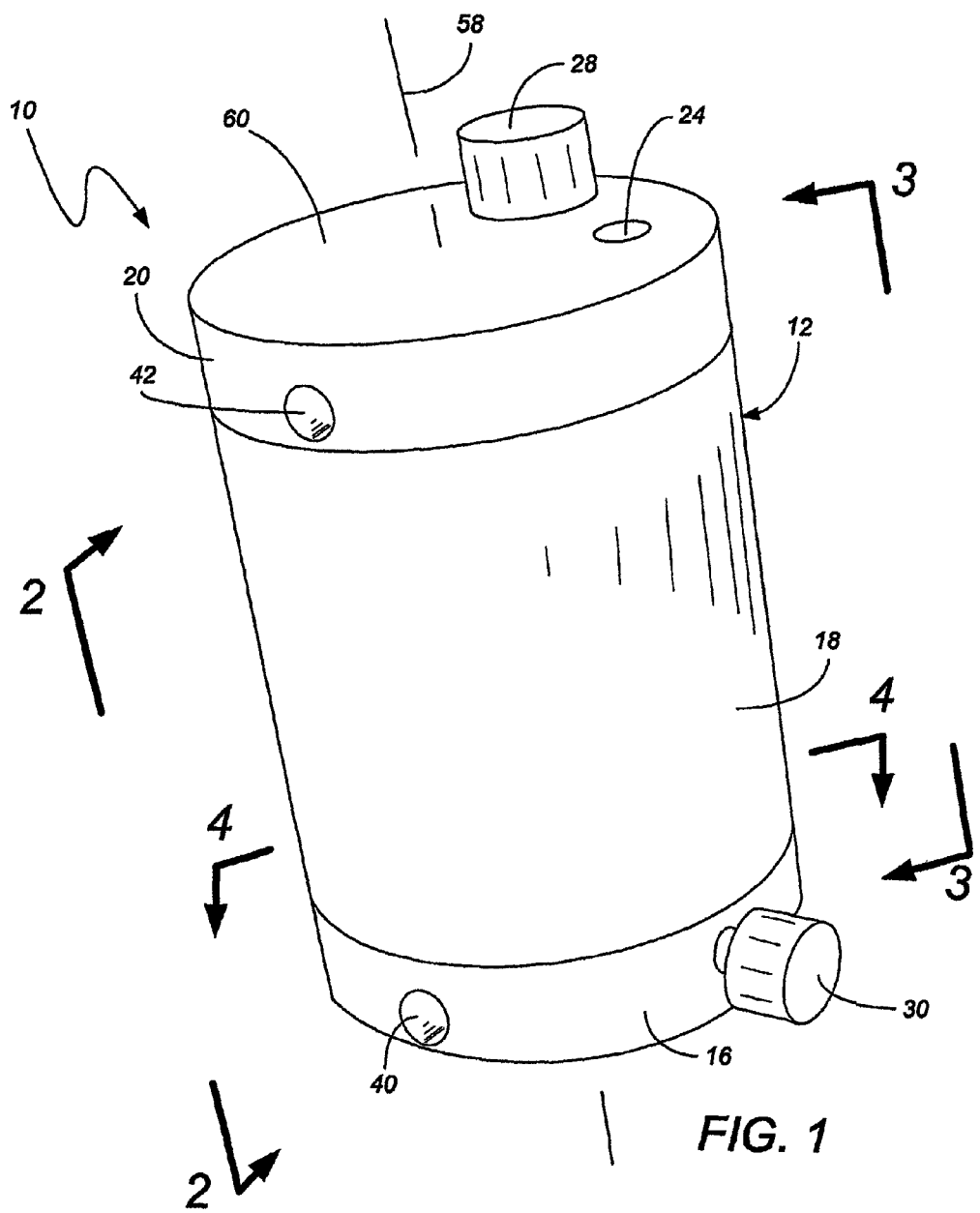
FIG. 1 is a perspective view of a first embodiment of the invention.

The concentrator 10 of the present invention primarily includes a main housing 12 which defines a centrifugation chamber 14. For ease of manufacture and assembly, the main housing 12 may be formed as a base plate 16, a central housing 18, and a top plate 20 as shown in FIG. 1. The main housing 12 is preferably molded of plastic, but could be formed of any sterilizable material. As part of manufacture and assembly, the base plate 16, central housing 18 and top plate 20 are preferably sealed to each other, such as through an epoxy sealant or sonic welding. The base plate 16, central housing 18 and top plate 20 may alternative be formed with mating threads so as to screw together, and sealed such as with a common O-ring.

In the preferred embodiment for use in treating blood, the central housing 18 is transparent or semi-transparent, thereby allowing viewing of the fluid contained within the centrifugation chamber 14 of the central housing 18. This allows viewing of the blood after centrifugation, to better determine which portion of the centrifuge separated blood to remove from the centrifugation chamber 14. Alternatively, the central housing 18 may include a window, i.e., a portion which is transparent or semi-transparent. When blood is placed into the blood centrifugation chamber 14 and centrifuged, color distinctions between the various components (platelet poor plasma, buffy coat and red cells) can be visually discerned. For fluids which do not visually separate during centrifugation, or if a float or other mechanism is used to determine which portion of the centrifuged fluid to remove from the centrifugation chamber 14, no window is necessary.

The overall size of the main housing 12 is selected to be compatible with existing centrifuges. For example, centrifuges are presently available which handle 4×4 inch vessels, and the main housing 12 is dimensioned to mate with and be received by the common 4×4 inch centrifuge (not shown). The bottom wall 22 of the base plate 16 is flat and includes no ports or items projecting from it, so the concentrator 10 can stand on a flat surface and will be stable during centrifugation.

The top plate 20 includes an opening 24 which serves as a fluid or blood inlet. The blood inlet 24 preferably includes a closure mechanism 26 (shown schematically in FIG. 3). The closure mechanism 26 could be a rubber stopper, with the blood hypodermically injected through the rubber stopper into the blood centrifugation chamber 14. However, the preferred closure mechanism 26 is a cap with a hand-turnable luer lock, commonly known in the blood handling art.

Figure 2:
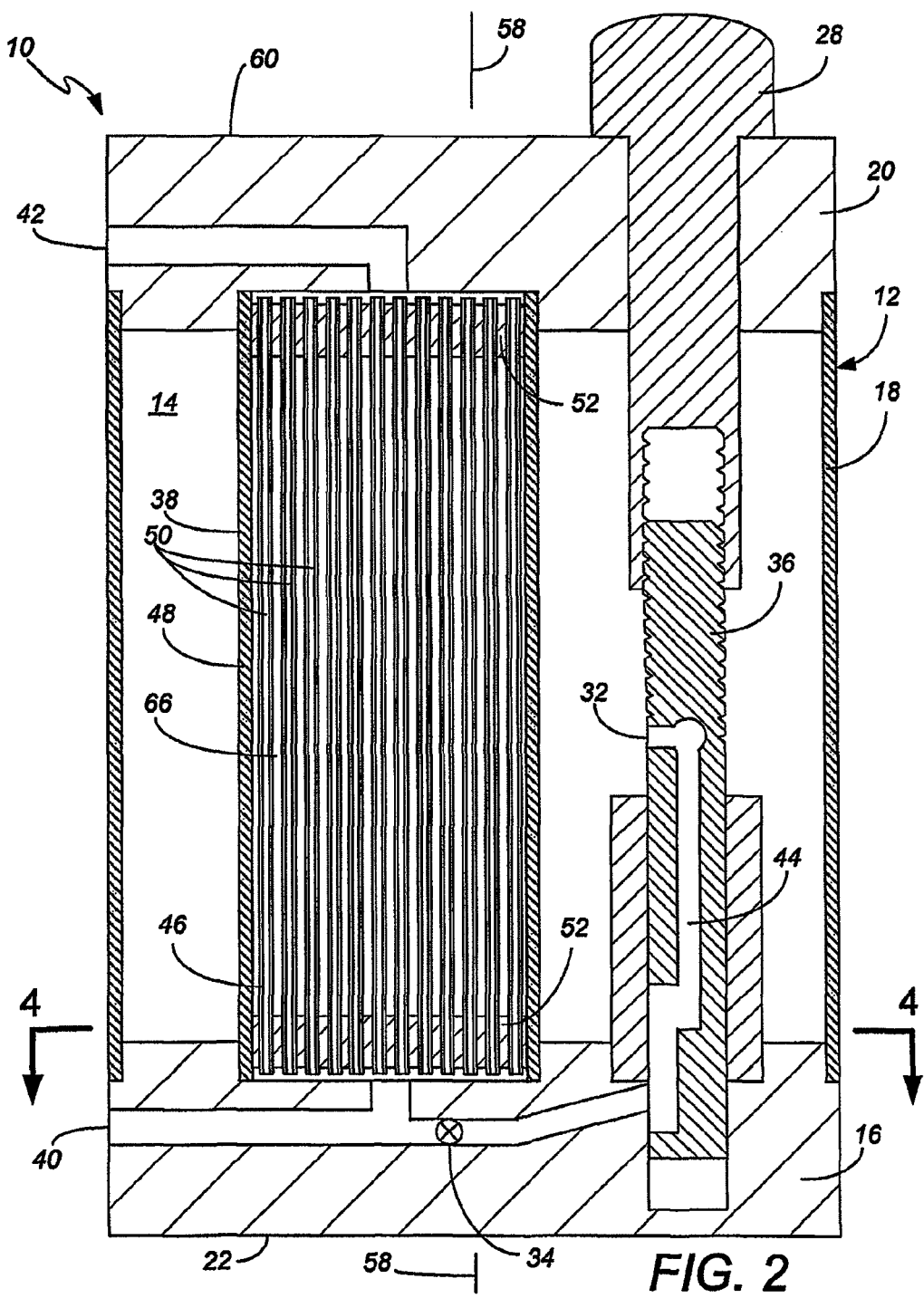
FIG. 2 is a cross-sectional side view of the embodiment of FIG. 1 taken along lines 2-2.

As shown in FIG. 1, a valve adjustment handle 28 is accessible in the top plate 20, and a valve control handle 30 is accessible in the base plate 16. These two handles 28, 30 control a valve inlet 32 and valve 34 (shown in FIG. 2) which are located within the concentrator 10. The valve adjustment handle 28 allows hand rotation of a threaded valve opening stem 36, the rotation of which changes the height of the valve inlet 32 relative to the main housing 12. As best shown in FIG. 2, the valve adjustment handle 28 is used to position the valve inlet 32 at a desired height to correspond with the height of the buffy coat or other desired fluid layer after centrifugation. The valve inlet 32 thus serves as the outlet port to remove a fraction of blood from the centrifugation chamber 14. While a threaded stem 36 provides an easy way of adjusting the height of the valve inlet 32, many equivalent mechanisms could be used such as a slide, float or other adjustment feature.

As shown in FIG. 2, a filter unit 38 is disposed within the centrifugation chamber 14. The filter unit 38 connects between a base port 40 defined in the base plate 16 and a top port 42 defined in the top plate 20. Piping 44 is included to transport the fluid from the valve inlet 32 to the base port 40 or inlet to the filter unit 38.

Figure 3:
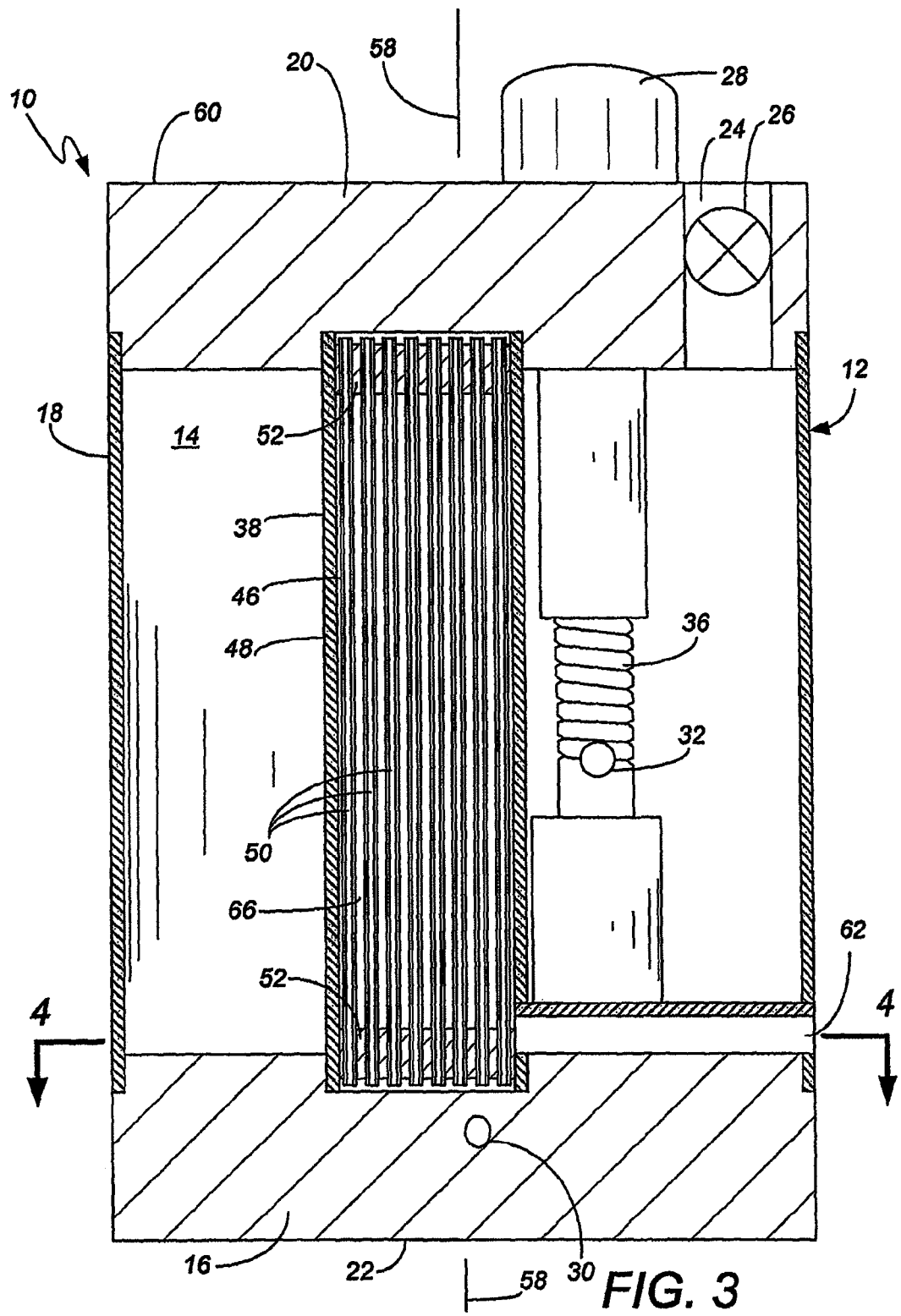
FIG. 3 is a cross-sectional side view of the embodiment of FIG. 1 taken along lines 3-3.
Figure 4:
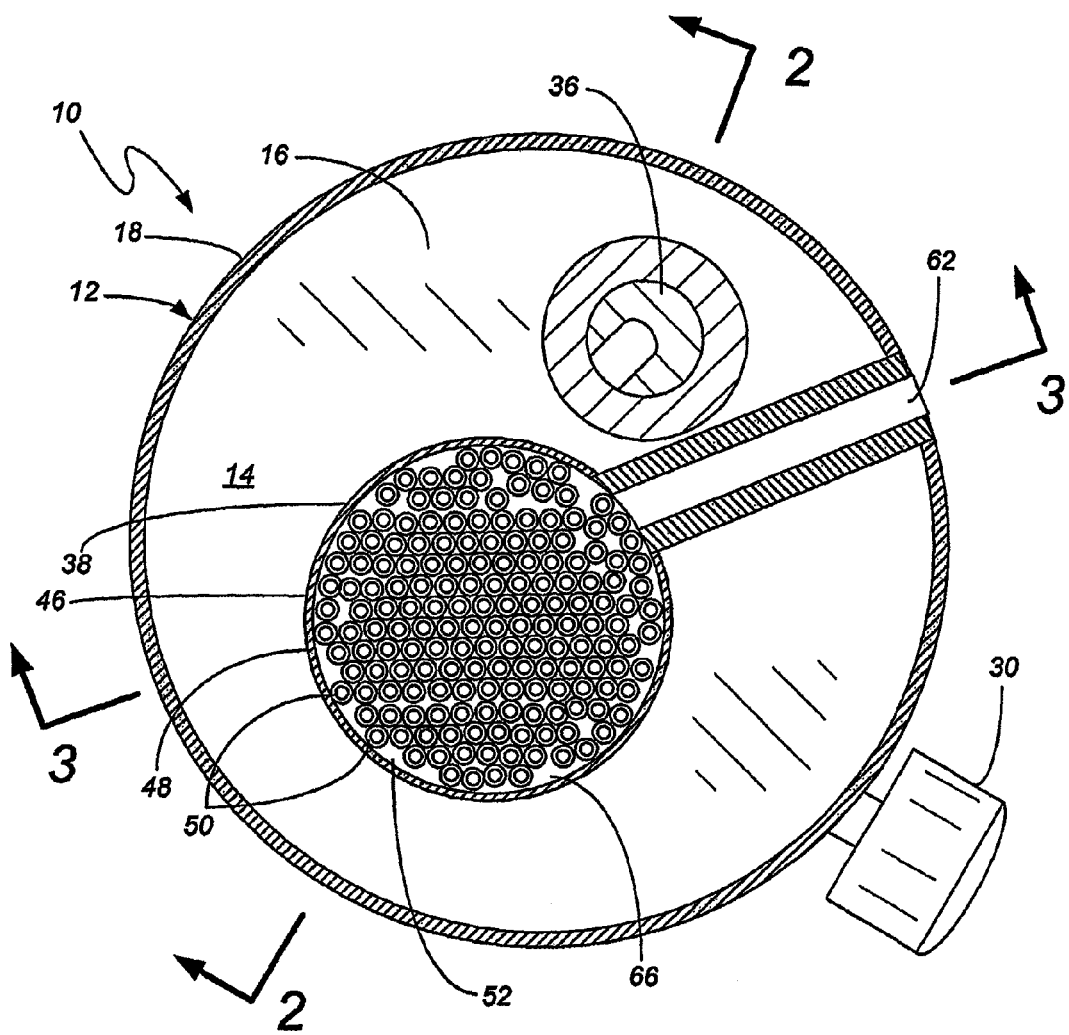
FIG. 4 is a cross-sectional plan view taken along line 4-4 in FIGS. 2 and 3.

As best shown in FIGS. 2-4, the preferred filter 46 includes a filter housing 48 and a large number of longitudinally oriented stranded filter lumens 50. The filter strands 50 are sealed with seals 52 to the filter housing 48 at each end. The preferred filter strands 50 are about 3½ inches long, with hundreds of filter strands 50 placed within a ¾ inch diameter filter housing 48, to provide a filter area of about 800 cm$^2$ or more. The filter strands 50 preferably have a pass size of about 10 to 30 kDalton through the lumen wall. With these filter strands 50, the filtrate or retentate moves longitudinally through the lumens 50 and through the filter housing 48, while water and low molecular weight components (generically called "permeate") pass through the filter membrane 50 transverse to the filter flow direction. Filter strands such as this may be available, for example, from Spectrum Labs of Rancho Dominguez, Calif. or Minntech of Plymouth, Minn.

The base port 40 and the top port 42 are in fluid communication with each other through the longitudinally oriented stranded filter lumens 50. If desired, the base port 40 and the top port 42 may include female threads (not shown) to receive transfer syringes 54, 56 shown in FIG. 5. The transfer syringes 54, 56 are used to apply hand controlled pressure to the centrifuged fluid to push/pull it through the filter 46. If desired, the base port 40 and the top port 42 may be recessed to allow the transfer syringes 54, 56 to extend inward to the location of the ends of the filter 46, thereby minimizing the piping distance (and piping volume) from the transfer syringes 54, 56 to the ends of the filter 46.

In the preferred embodiment, the base port 40 and the top port 42 are disposed on the side of the concentrator 10, oriented transverse to the longitudinal axis 58. This placement allows the base port 40 to be accessible while the concentrator 10 is standing upright on the bottom wall 22 of the base plate 16, and allows the top port 42 to help balance the base port 40 during transfer of the fluid component through the filter 46. Alternatively, the base port 40 and the top port 42 could be slanted relative to the longitudinal axis 58, or even extend through the bottom wall 22 of the base plate 16 and top wall 60 of the top plate 20 parallel to the longitudinal axis 58. Placement of the ports 40, 42 parallel to the longitudinal axis 58 would align the syringe plunger strokes with the direction of blood movement through the filter 46, thereby reducing the pressure loss due to piping turns and thereby reducing the risk of damaging the blood during use of the concentrator 10.

Figure 5:
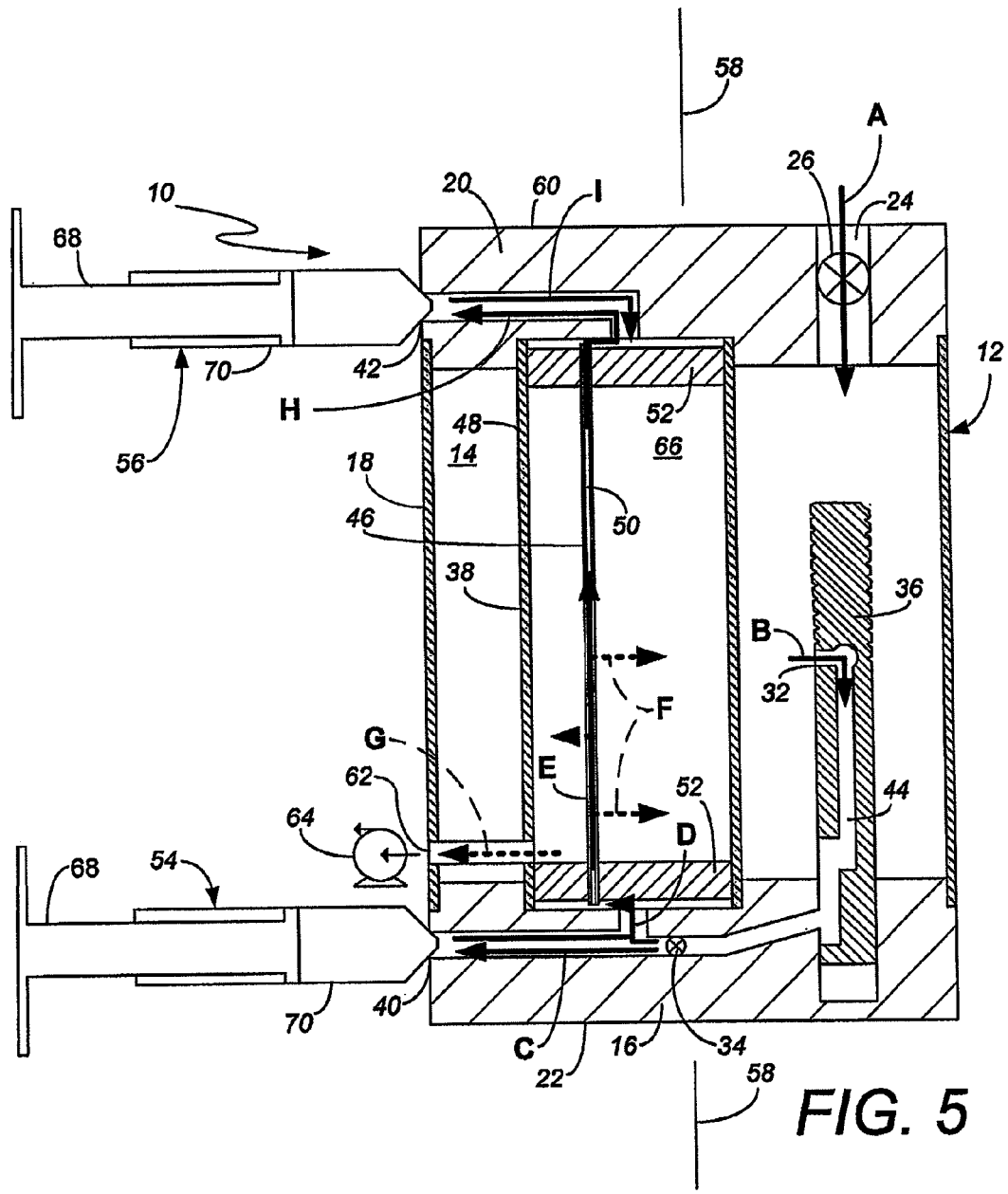
FIG. 5 is a side view of FIGS. 2 and 3, simplified and modified so as to show all functions on a single view, with arrows A-I indicating the stepwise handling of the body fluid through the inventive device.

As shown in FIGS. 3-5, a vacuum port 62 connects through the main housing 12 and through the filter housing 48. With the vacuum port 62, vacuum pressure 64 (shown schematically in FIG. 4) can be applied to the exterior of the filter strands 50 while the blood component passes through the filter lumens 50. Vacuum sources 64 are commonly available in environments where the concentrator 10 is utilized. If no vacuum source 64 is available, the vacuum port 62 still serves as a gravitational drain to remove water and low molecular weight components that have passed through the filter membrane 50. To help vacuum port 62 act as a gravitational drain, it is placed at the bottom of the filter chamber 66.

In the preferred embodiment, the filter housing 48 is sealed to eliminate fluid communication between the centrifuge chamber 14 and the filter chamber 66. Alternatively, the filter housing 48 may be open to the centrifuge chamber 14, such that the water and low molecular weight components which pass through the filter membrane 50 proceed into the centrifuge chamber 14. Because the red blood cells centrifuge-separated from the buffy coat are generally discarded, the addition of the water and low molecular weight components to the red blood cells is inconsequential. If the filter housing 48 permits fluid communication between the filter chamber 66 and the centrifuge chamber 14, then the vacuum port 62 will serve to remove or drain red blood cells as well as water and low molecular weight components from the concentrator 10.

The use of the invention is described with respect to the lettered steps shown in FIG. 5. First, a unit of blood (approximately 60 to 80 ccs) is placed through the inlet closure 26 and into the centrifugation chamber 14 as shown by arrow A. Preferably, this occurs within minutes after the blood is withdrawn from the patient. Different amounts of blood or different types of fluid can be alternatively used if the concentrator 10 is used for a different concentration purpose.

Once the entire blood unit is within the centrifugation chamber 14, the inlet closure 26 is closed, and the concentrator 10 is centrifuged. The centrifugation process is performed in accordance with known centrifuge strategies and velocities.

After centrifugation is complete, the blood has separated into different layers of red cells, buffy coat and platelet poor plasma, which are visually discernable by viewing through the central housing 18. Transfer syringes 54, 56 are attached to the base port 40 and the top port 42. The valve adjustment handle 28 is rotated until the height of the valve inlet 32 lines up with the bottom of the fluid layer(s) desired to be further processed, in this case the bottom of the buffy coat. The valve 34 is opened using the valve control handle 30, while the desired fluid layer(s) (buffy coat and preferably also platelet poor plasma) drains into the base plate 16 and the bottom syringe 54 as shown by arrows B and C. If necessary for pressure relief to enable all of the desired fluid layers to be removed from the centrifuge chamber 14, the inlet closure 26 may be opened slightly during draining of the desired fluid layers through the valve 34. Preferably, however, the inlet closure 26 will incorporate a valve (not shown) allowing for pressure release. Once the desired fluid layer(s) have been extracted, the valve control handle 30 is used to close off the valve 34. The unwanted layers (red cells, and preferably platelet poor plasma) are retained in the centrifugation chamber 14.

Vacuum pressure is now applied to the vacuum port 62. Because the remainder of the concentration procedure does not rely on gravitational weight separation, the concentrator 10 device may be placed on its side if desired. The vacuum port 62 is preferably located on a side of the central housing 18 opposite the transfer ports 40, 42, thereby providing counterweight and stabilization during transfer of the desired fluid layer(s) through the filter 46. The plunger 68 on the bottom syringe 54 is pushed (while the plunger 68 on the top syringe 56 is optionally being pulled), pushing the desired fluid upward and into the top syringe 56 as shown by arrows D and E. Water and low molecular weight elements of the desired fluid (buffy coat/platelet poor plasma) are removed through the filter strands 50, as shown by arrows F, and then drained through the vacuum port 62 as shown by arrow G. The desired fluid passes through the filter strands 50 and into the top syringe 56 as shown by arrow H, becoming "first pass concentrated".

In the first preferred embodiment, the volume of the piping 44 from the valve inlet 32 to the filter 46, including the bottom syringe 54, is minimized so as to get as great a yield of concentrated desired fluid (concentrated buffy coat/platelet poor plasma) from a single starting (whole blood) unit as possible. If desired, the top port 42 and the base port 40 may include recesses to receive a greater length of the transfer syringes 54, 56, and thereby minimize the distance from the end of the transfer syringes 54, 56 to the inlets to the filter housing 48.

In most instances, further concentration of the first pass concentrated fluid will be desired by reverse filtering. The plunger 68 on the top syringe 56 is pushed (while the plunger 68 on the bottom syringe 54 is optionally pulled), thereby pushing the first-pass concentrated fluid through the filter 46 as shown by arrow I and into the bottom syringe 54. Additional water and low molecular weight components are withdrawn from the first-pass concentrated fluid (arrows F and G). The reverse filtering makes additional use of the filtration strands 50 and further concentrates the first pass concentrated fluid into "second pass concentrated" fluid. If desired, additional passes may be performed in a like manner. The most preferred method utilizes "four pass concentrated" buffy coat/platelet poor plasma.

The concentrated fluid may be used immediately (directly applied to wound site) or after further preparation such as mixing the concentrated fluid with thrombin and an artificial bone substance or mixing the concentrated fluid with thrombin and then brushing it onto an implant's surface.

The stranded filters 50 used within the preferred embodiment are single use filter elements, which cannot be effectively cleaned and sterilized. Accordingly, the filter element 46 is disposed of after its single use. In the preferred embodiment, the entire centrifugation/filtering vessel 10 is sufficiently inexpensive that the entire concentrator 10 unit can be discarded after a single use. This simplifies and/or avoids cleaning of the centrifugation unit and/or filter housing 48. This also simplifies disposal of the unneeded blood components.

Filtering within the centrifuge vessel provides further advantages which can be achieved in alternative embodiments. For instance, if the inlet 32 for the drain valve 34 is automatically (rather than visually) positioned at the proper height for the desired fluid layer(s), then the drain valve 34 could be automatically opened using centrifugally activated valves as known in the art. Using similar arrangements, the desired fluid layer(s) can be passed through the filter 46 during centrifugation, using centrifugal forces to push/pull the desired fluid layer(s) through the filter 46.

The preferred filter 46 is oriented longitudinally with respect to the centrifugation direction (i.e., with respect to longitudinal axis 58). This helps minimize the possibility that the filter strands 50 might pull from their end seals 52 and/or break during centrifugation. Alternative embodiments could include orienting the filter strands 50 transversely and at the general height of the desired fluid layers, thereby further reducing the piping volume needed to transfer the desired fluid layer(s) coat to the filter 46.

The preferred embodiment utilizes external syringes 54, 56 to provide the transfer pressure force for pushing/pulling the desired fluid layer(s) through the filter 46. This provides a lowest cost method of applying such forces. The syringes 54, 56 also permit the surgeon to control the amount of pressure versus time (i.e., the pressure-time curve witnessed by the buffy coat/platelet poor plasma) on the filtration chamber 66 to force a selected amount of water and low molecular weight components of the centrifuged blood fraction through the filter membrane 50. As an alternative to the use of external syringes, the syringes 54, 56 (including particularly the plunger 68 and slide tube elements 70) could be fabricated and/or attached as part of the device. For instance, the bottom wall 22 of the base plate 16 and the top wall 60 of the top plate 20 could be slidable or depressible similar to the plunger on a syringe, to thereby apply the transfer pressure to push/pull the desired fluid layer(s) through the filter 46. The use of syringes 54, 56 also allows for the force pushing the desired fluid layer(s) through the filter 46 to be hand controlled by the surgeon or other operator.

Figure 6:
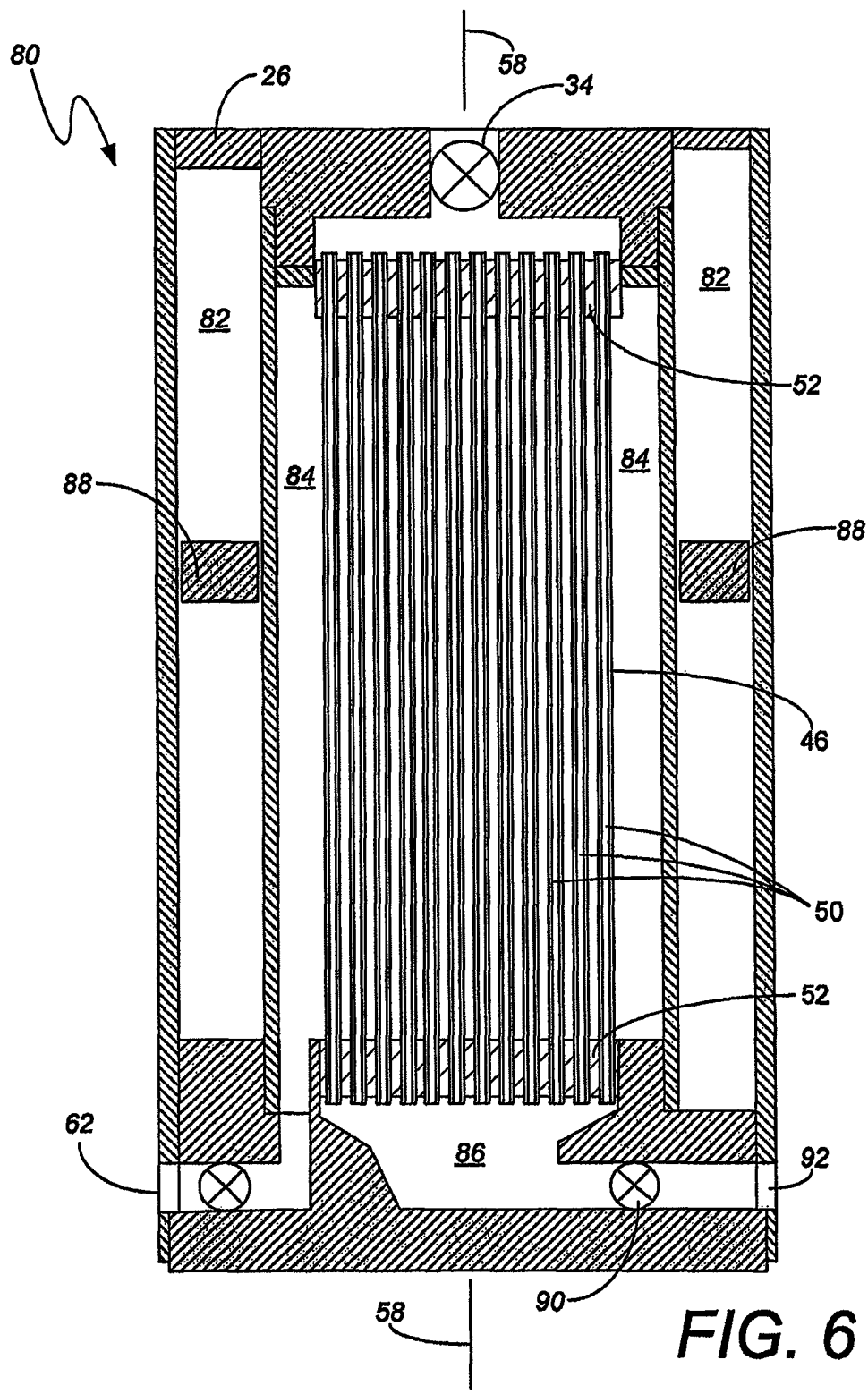
FIG. 6 is a cross sectional side view of a second embodiment of the invention.

An additional embodiment of the invention is shown in the concentrator 80 of FIG. 6. Similar to the first embodiment 10, the same vessel used in the centrifuge is also used to provide filtration. That is, blood is centrifuged in the concentrator vessel 80, and then positive or negative pressure is applied in the same concentrator vessel 80 after centrifugation to force water and/or low molecular weight components ("water") from the buffy coat/platelet poor plasma centrifuged fraction resulting in a first pass concentrated component.

The concentrator vessel 80 includes three chambers 82, 84, 86. A centrifuge chamber 82 holds the fluid during centrifugation. A water chamber 84 receives water and low molecular weight components removed from the desired fluid layer(s)

through the filter 46. A concentrated fluid chamber 86 receives the concentrated fluid which has been filtered.

The centrifuge chamber 82 preferably holds a float 88 of a particular specific gravity, such as generally equal to the specific gravity of buffy coat. The float 88 can be used to aid in positioning of a syringe (not shown) during transfer of the desired fluid layer(s) from the centrifuge chamber 82 to the filter 46. Alternatively, openings in the float 88 can be provided to permit blood fraction flow therethrough during centrifugation.

The "shut off" valve 90 for the concentrated fluid chamber 86 may be a variable position valve that would allow the operator to "dial in" the maximum pressure that could be generated in the concentrated fluid chamber 86, and/or the maximum pressure differential between the water chamber 84 and the concentrated fluid chamber 86, thereby controlling the concentration of the final output. For example, the shut off valve 90 may include a dial with three or more positions connected to something like a butterfly valve or regulator valve, such that the operator selects the desired concentration on the dial then pressurizes the desired fluid layer(s) through the filter 46 to the selected pressure/concentration level. Depending on the dial position selected, a predetermined pressure is generated across the filter 46 that allows for the corresponding amount of water to be removed, thus delivering the desired concentration in one stroke and without the need to fully close off the outport 92.

Figure 7:
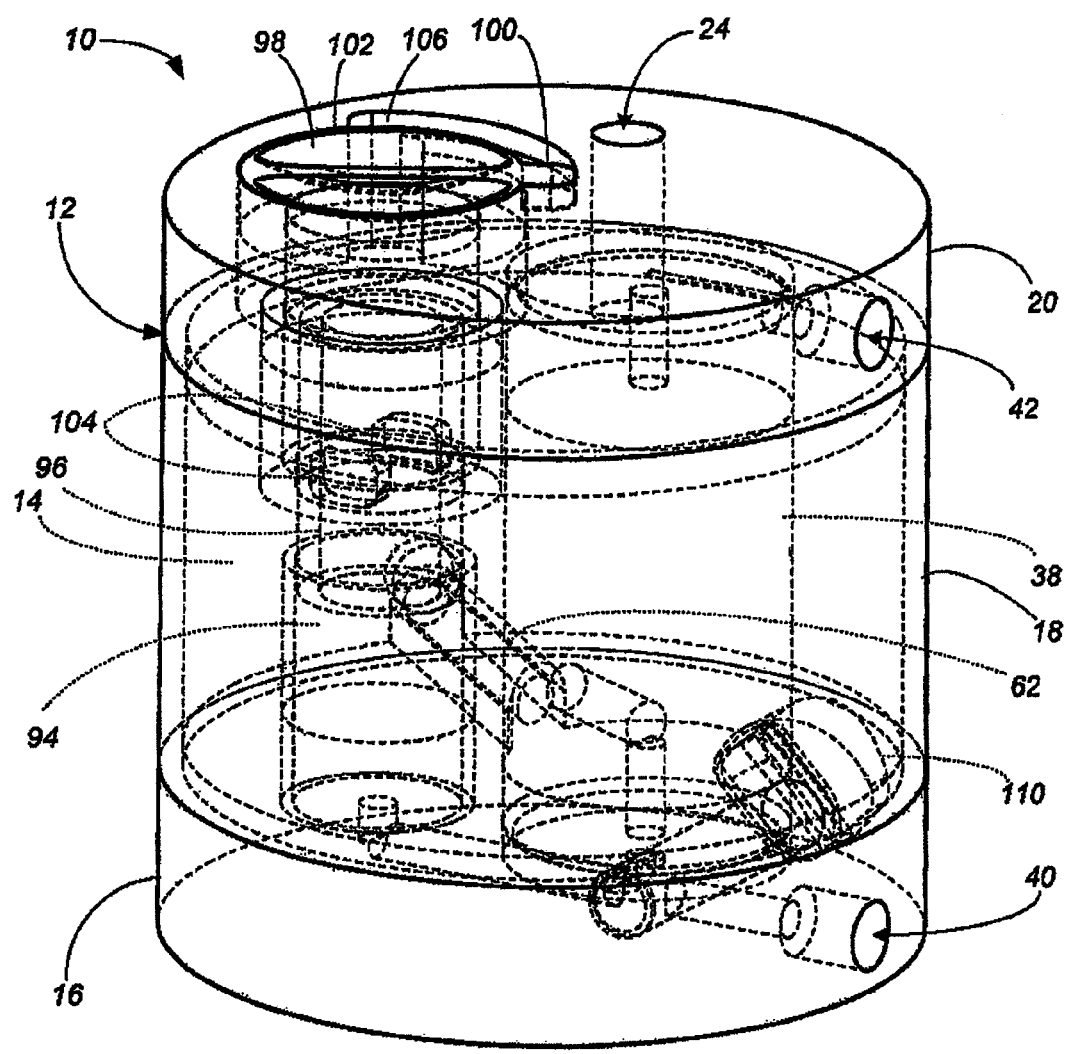
FIG. 7 is a perspective view of a third embodiment of the invention, showing hidden detail in dashed lines.
Figure 8:
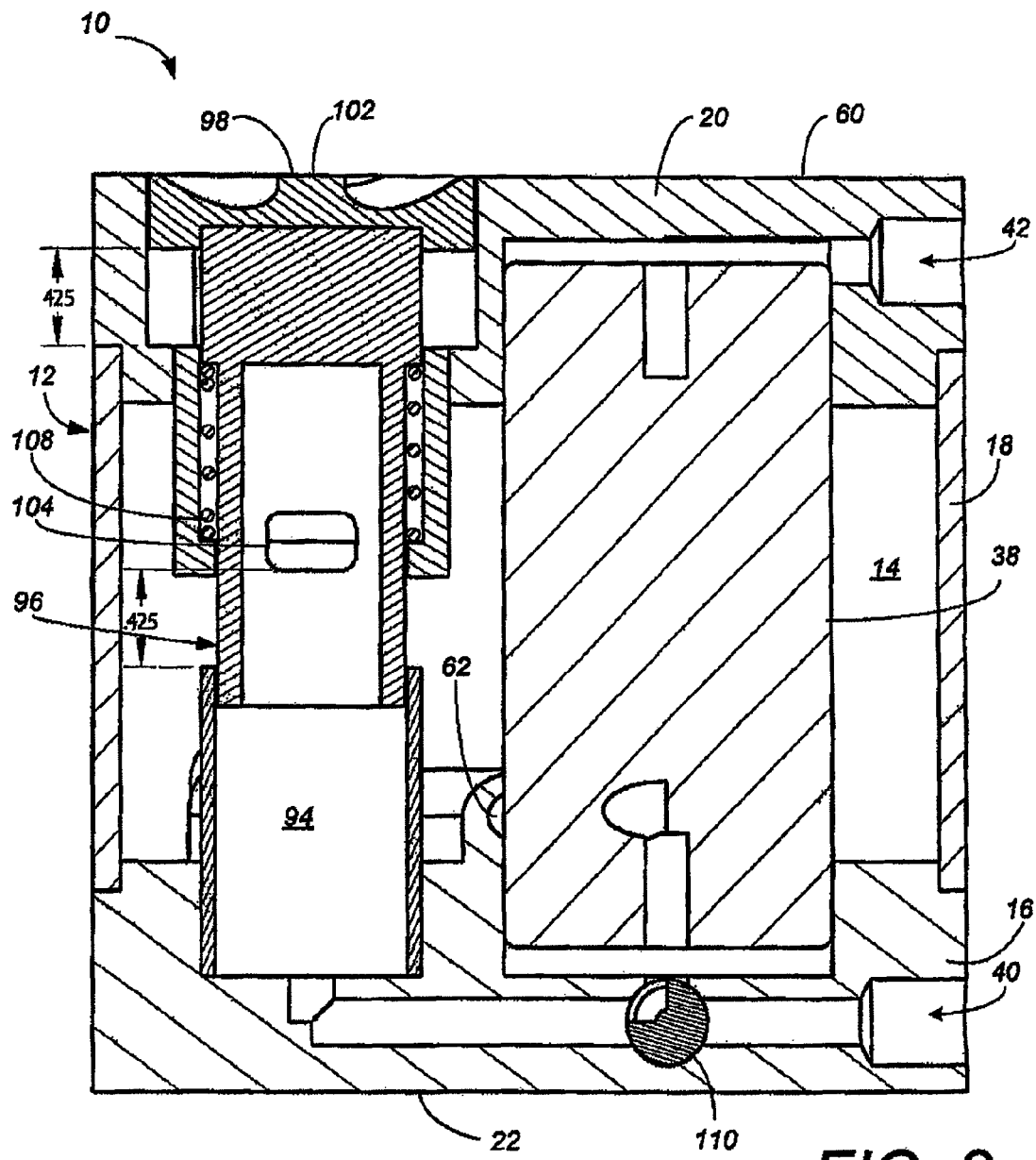
FIG. 8 is a cross-sectional view of the embodiment of FIG. 7

In a third embodiment shown in FIGS. 7 and 8, a desired fluid layer(s) isolation chamber 94 is defined between the centrifugation chamber 14 and the filter unit 38. Also, a window valve 96 is added between the centrifugation chamber 14 and the isolation chamber 94. The window valve 96 is ordinarily closed, preventing fluid communication between the centrifugation chamber 14 and the isolation chamber 94. Thus, while the starting fluid (whole blood) is in the centrifugation chamber 14 and during centrifuging, there is no possibility of the starting fluid passing through the window valve 96 and into the isolation chamber 94 (or into other piping between the centrifugation chamber 14 and the filter unit 38 such as piping 44 in the first embodiment).

The preferred window valve 96 has a locking mechanism 98, which also acts as a valve handle. A lock 100 prevents the lock handle knob 102 from being pushed down, thereby preventing the windows 104 from being pushed down into communication with the centrifugation chamber 14 during centrifugation. Once centrifugation is complete, the lock handle knob 102 is rotated 90° to a position where the lock 100 lines up with a keyway 106, enabling the knob 102 to be pushed downward against a spring 108. The windows 104 are attached to and controlled by the knob 102, and pushing the lock handle knob 102 downward moves the windows 104 downward into communication with the centrifugation chamber 14. When the windows 104 are open to the centrifugation chamber 14, the desired fluid layer(s) (buffy coat and preferably also platelet poor plasma) of the centrifuged fluid flow by gravity from the centrifugation chamber 14 into the isolation chamber 94. Once the desired fluid layer(s) have drained into the isolation chamber 94, the knob 102 is released, with the spring 108 moving the windows 104 upward and closing communication between the isolation chamber 94 and the centrifugation chamber 14.

The isolation chamber 94 holds the desired fluid layer(s) until subsequent processing, such as filtration. The isolation chamber 94 defines the volume of the desired fluid layer(s) which will be removed from the starting fluid unit and filtered. Placement of the desired fluid layer(s) within the isolation chamber 94 allows the concentrator 10 to be handled without fear of remixing the desired fluid layer(s) into the remainder of the starting fluid. For instance, after the buffy coat and platelet poor plasma is within the isolation chamber 94, the concentrator 10 can be placed on its side before attaching syringes 54, 56 into the filter transfer ports 40, 42 for filtering.

The isolation chamber 94 also permits a delay time between centrifugation and filtering. The desired fluid layer(s) can optionally be further treated while in the isolation chamber 94. For example, blood additives may be added to the fluid within the isolation chamber 94, particularly if the blood additives enhance the filtration process, such as by having the blood additives in the isolation chamber 94 prior to opening the window valve 96.

A twist valve 110 is opened to open communication between the isolation chamber 94 and the base port 40 and the filter unit 38. The desired fluid layer(s) (buffy coat/platelet poor plasma) are withdrawn from the isolation chamber 94 through the twist valve 110 with a syringe 54, at which point the twist valve 110 is closed. The plunger stroke on the syringe 54 is then reversed to push the desired fluid layer(s) through the filter unit 38. If desired, the syringes 54, 56 for pressuring the fluid layer(s) through the filter unit 38 can have a much lower volume than the isolation chamber 94 (say, for instance, ⅓ the volume). Then fluid can be removed from the isolation chamber 94 in portions (⅓ at a time) which are filtered separately, one portion at a time. Portioning of the desired fluid layer(s) through the filter unit 38 is particularly advantageous in situations wherein preparation steps are taken for the filter 46 between portions. For instance, if the filter 46 is becoming clogged while only filtering ⅓ of the fluid volume in the isolation chamber 94, a purge fluid could be pressured through the filter 46 to unclog the filter 46 prior to filtering the second portion through the filter 46. After the first portion has been filtered and the filter 46 purged, the twist valve 110 is reopened to remove a second portion. The twist valve 110 is then reclosed to permit filtering of the second portion, followed by any purging of the filter 46. Because the twist valve 110 controls communication between the isolation chamber 94 and the base port 40, fluid may thus be removed from the isolation chamber 94 in whatever size portions are desired.

In another embodiment (not shown), a syringe having a plunger is provided to pull the component (i.e., buffy coat/platelet poor plasma under negative pressure) out of the centrifuged starting fluid (whole blood). The syringe also houses a filter 46, and the plunger stroke is reversed to push (use positive pressure) the component through the filter 46 and separate the component into water and a concentrated retentate.

In all these embodiments, the surgeon preferably controls the pressure and/or duration of the filtration step, and thus the surgeon controls how concentrated the concentrated retentate (buffy coat/platelet poor plasma) is relative to the centrifuged component, as well as how hard the fluid is worked during the filtration step.

Although the present invention has been described with reference to preferred embodiments, workers skilled in the art will recognize that changes may be made in form and detail without departing from the spirit and scope of the invention. For instance, while the invention has been described with regard to producing a concentrated buffy coat/platelet poor plasma component from blood, it could also be used for centrifugation/filtration of other fluids. The specific dimensions and materials mentioned but not required by the claims are exemplary only, and do not limit the claimed invention.

The invention claimed is:

1. A concentrator for biological fluids, comprising:
   a top plate and an oppositely disposed base plate;
   a separation chamber for holding the biological fluid, wherein the separation chamber includes a longitudinal axis and is connected to the base plate and top plate such that the separation chamber is disposed between the base plate and the top plate;
   a flow passage from an outlet port in the separation chamber to a base port in the base plate, the flow passage comprising a length wherein the outlet port is adjustably positionable along the longitudinal axis such that the length of the flow passage changes relative to the position of the outlet port along the longitudinal axis; and
   a valve opening stem in the separation chamber, wherein the valve opening stem comprises the outlet port and rotation of the valve opening stem changes the height of the outlet port along the longitudinal axis of the chamber.

2. The concentrator of claim 1, further comprising an adjustable flow control valve in fluid communication with the flow passage.

3. The concentrator of claim 1, wherein the valve opening stem is connected to a valve adjustment handle.

4. The concentrator of claim 3, wherein the top plate comprises the valve adjustment handle.

5. The concentrator of claim 1, wherein the concentrator is configured for application of a separation force to the concentrator such that biological fluid in the separation chamber separates into component layers along the longitudinal axis of the separation chamber upon application of the separation force to the concentrator.

6. The concentrator of claim 5, wherein the separation force is generally parallel to the longitudinal axis.

7. The concentrator of claim 5, wherein the biological fluid separates into component layers generally orthogonal to the longitudinal axis upon application of the separation force.

8. The concentrator of claim 5, wherein the separation force comprises centrifugation.

9. The concentrator of claim 5, wherein the outlet port is adjustably positionable to permit selection of component layers along the longitudinal axis for extraction from the separation chamber.

10. The concentrator of claim 1, wherein the flow passage comprises piping.

11. The concentrator of claim 1, wherein the top plate comprises a top port for introducing the biological fluid into the separation chamber.

12. The concentrator of claim 11, wherein the top port and base port are configured to mate with a syringe.

13. The concentrator of claim 1, wherein the separation chamber comprises a chamber wall at least a portion of which is translucent.

14. A method of concentrating a component from a fluid with an apparatus of claim 1, comprising:
    separating the fluid in said separation chamber to form component layers along said longitudinal axis;
    adjusting the outlet port along the longitudinal axis to select a component layer; and
    extracting a portion of the selected component layer from said separation chamber through the outlet port.

15. The method of claim 14, wherein adjusting the outlet port comprises positioning the outlet port along said longitudinal axis such that the outlet port is in fluid communication with the selected component layer.

16. The method of claim 14, wherein separating comprises applying a separation force to the concentrator such that the fluid separates into component layers generally orthogonal to the longitudinal axis.

17. The method of claim 16, wherein the separation force comprises centrifugation.

18. The method of claim 14, where the fluid is blood.

19. The method of claim 14, wherein the component is plasma.

20. The method of claim 19, wherein the plasma is platelet rich plasma.

21. The method of claim 19, wherein the plasma is platelet poor plasma.

* * * * *